United States Patent [19]

Edwards, III et al.

[11] Patent Number: 5,028,591

[45] Date of Patent: Jul. 2, 1991

[54] METHOD FOR STIMULATING THE IMMUNE SYSTEM

[75] Inventors: Carl K. Edwards, III; Libby M. Yunger, both of Terre Haute, Ind.

[73] Assignee: Pitman-Moore, Inc., Lake Forest, Ill.

[21] Appl. No.: 321,594

[22] Filed: Mar. 9, 1989

Related U.S. Application Data

[63] Continuation of Ser. No. 95,986, Sep. 14, 1987, Pat. No. 4,837,202.

[51] Int. Cl.$^5$ .............................................. A61K 37/36
[52] U.S. Cl. .......................................... 514/12; 514/2; 514/21; 514/885
[58] Field of Search ......................... 514/12, 21, 2, 885

[56]  References Cited

U.S. PATENT DOCUMENTS 4,814,323  3/1989  Andriue ................................ 514/11
4,837,202  6/1989  Edwards, III ........................ 514/12

FOREIGN PATENT DOCUMENTS 0085036  8/1983  European Pat. Off. .

OTHER PUBLICATIONS

Alberts et al., *Molecular Biology of the Cell*, Garland Publishing Inc., N.Y. 1983, pp. 919, 951-954.
Edwards et al., *Society for Leukocyte Biology* (Res. Soc.), Marco Island, FA, Oct. 12-15, 1989. Abstract
Kelly et al., *Proceedings of an International Symposium*, Dec. 12-14, 1988, 145-153, Effect of Somatotropin on the Immune System.
Shemerovskaya et al., *Byull. eksper, Biol.* (USSR) 5:78-80, 1975 (English Translation).
Stebbing, *Proceedings of the 19th Annual Miami Winter Symposium*, Academic Press, N.Y., 445-458 (1952).
Shemerovskaya, *Chem. Abst.*, 83, 135 (1975). Abst. No. 72471r.
Anderson, *J. Endocr.*, 68, 345-346 (1976).
Jaroff, *Time*, 56-64, May 23, 1988, Stop That Germ!
Goodman et al., *The Pharmaceutical Basis of Therapeutics*, Third Ed., The Macmillan Co., N.Y., pp. 992-993, 1965.

*Primary Examiner*—F. T. Moezie
*Attorney, Agent, or Firm*—Wendell Ray Guffey; Thomas L. Farquer

[57] ABSTRACT

The proteins somatotropin and prolactin are administered to animals in amounts of from about 0.1-24 mg/animal/day to stimulate the immune system by increasing the production of macrophages and augmenting the oxidative metabolism of macrophages. The activated macrophages combat infectious disease causing agents such as viruses, bacteria, fungi, protozoa, helminths, and the like and thus are effective in preventing and treating diseases caused by those agents.

7 Claims, No Drawings

METHOD FOR STIMULATING THE IMMUNE SYSTEM

This application is a continuation of Ser. No. 095,986, filed Sept. 14, 1987, now U.S. Pat. No. 4,837,702.

This invention relates generally to methods for stimulating the immune system in animals and particularly to methods for using the proteins somatotropin or prolactin to stimulate the immune system by increasing the production of macrophages and augmenting the oxidative metabolism of macrophages.

BACKGROUND OF THE INVENTION

1. The Compounds a. Somatotropin

The isolation, purification and properties of somatotropins are well known in the art. Generally, somatotropin (ST), sometimes referred to as growth hormone (GH) in the art, is produced by the pituitary throughout an animal's life, although apparently in higher amounts during the pre-adult period. ST is known to promote skeletal growth, nitrogen retention, protein synthesis and to affect glucose and lipid metabolism. Accordingly, ST is recognized as a general anabolic agent.

ST can be isolated from excised pituitary tissue. See, e.g., C.H. Li, *J. Biol. Chem.* 211, 55 (1954). ST can also be obtained from genetically engineered microorganisms containing recombinant DNA which specifies the production of ST. See, e.g., P.H. Seeburg, et al., *Nature*, 276, 795-798 (1978); P.H. Seeburg et al., *Nature*, 270, 486-494 (1978); J.A. Martial, *Science*, 205, 602-607 (1979).

Somatotropins from particular species have been studied and characterized. For example, bovine somatotropin (bST) is known to be a polypeptide synthesized in and secreted from the anterior lobe of the pituitary. A nucleotide coding sequence and an amino acid sequence of native bST have been reported; e.g. W.L. Miller et al., *J. Biol. Chem.*, 255, 7521-24 (1980); M. D. Dayhoff et al., in "Atlas of Protein Sequence And Structure", Dayhoff ed., 5, Supp. 3, 345-42 (1978); and M. Wallis, *FEBS Lett*, 35, 11-14 (1973). bST is a protein of 191 amino acids and appears to be synthesized initially as a bovine pre-somatotropin of 217 amino acids; the signal sequence of 26 amino acids being removed from the N-terminal position during synthesis and secretion, e.g. V.R. Lingapa et al., *Proc. Natl. Acad. Sci. USA*, 74, 2432-36 (1977).

The preparation of bST is well known in the art. For example, bST is extracted from pituitary glands of cattle or produced via recombinant DNA technology in appropriate hosts, e.g., W.L. Miller et al., *J. Biol. Chem.*, 255, 7521-24 (1980). U.S. Pat. No. 4,443,539 to Frazier et al, discloses a process for preparing bST by utilizing recombinant DNA methodology to place the bST structural gene into yeast cells. U.S. Pat. No. 4,371,462 to Hecht, discloses a method for the purification of anterior pituitary peptides. European Patent Application Nos. 83304574.3, filed Aug. 8, 1983, with Publication Number 103,395; 82304880.6, filed Sept. 16, 1982, with Publication Number 075,444; and 81303824.7, filed Aug. 21, 1981, with Publication Number 047,600; and British Patent Application No. 2,073,245A disclose methods for producing recombinant bST in high yields. Strains of *E. Coli* that produce bST are available from the American Type Culture Collection under accession numbers ATCC 31826, 31840, 31841, 31842, and 31843.

Similarly, the preparation of natural and recombinant porcine and human somatotropin is well known. For example, in addition to the publications above which disclose methods for obtaining the porcine and human somatotropin, U.S. Pat. No. 4,604,359 discloses methods for the microbial expression of human somatotropin; U.S. Pat. No. 4,332,717 discloses methods for the purification of human somatotropin; and European Patent Application No. 83305717.7, filed Sept. 26, 1983, with Publication Number 104,920, discloses methods for producing recombinant porcine ST in high yields. Many other such publications and methods are well known to skilled artisans.

b. Prolactin

Prolactin (PRL) is a 199 amino acid protein which is normally produced by the pituitary throughout an animal's life. PRL plays a role in the development of mammary tissue in females and, during pregnancy, produces a further development of mammary tissue and stimulates the production of milk. Although known for its mammatropic and lactogenic effects, PRL is generally not considered an efficient anabolic agent.

PRL has been isolated from excised pituitary tissue. See, e.g., Li et al., *Nature*, 224, 695-696 (1963) (ovine); Lewis et al., *Biochem. Biophys. Res. Commun.*, 44(5), 1169 (1971) (human); Reisfeld et al., *J. Am. Chem. Soc.*, 83, 3719 (1961) (sheep); and Li et al., *J. Biol. Chem*, 146, 627 (1942). PRL can also be obtained from genetically engineered microorganisms containing recombinant DNA which specifies the production of PRL using well known techniques; for example, U.S. Pat. No. 4,666,839 to Souza discloses a method for preparing bovine prolactin (PRL) by utilizing recombinant DNA methodology. A nucleotide coding sequence and an amino acid sequence of native bPRL have been reported; e.g. W.L. Miller et al., *J. Biol. Chem.*, 255, 7521-24 (1980).

Similarly, porcine prolactin (pPRL) can be extracted from pituitary glands of swine or can be produced via recombinant DNA technology in appropriate hosts by means well known to skilled artisans. U.S. Pat. Nos. 3,317,392 to Eppstein and 3,265,580 to Nelson et al, disclose processes for preparing porcine prolactin from porcine pituitary glands. PRL can be purchased commercially from the UCLA Medical School.

Although somatotropin and prolactin have been recognized for their anabolic and mammotropic/lactogenic activity respectively, these proteins have not generally been recognized as immunostimulating agents which activate macrophages and increase an animal's resistance to disease.

2. Diseases and the Immune System

Animals are susceptible to many diseases caused by viruses, bacteria, fungi, protozoa, helminths, and other disease causing agents. Exposure to these disease causing agents is inevitable; often arising from the animal's natural environment. Commercial farm animals such as cattle, sheep, poultry, swine, and the like are exposed to many disease causing agents during the process involved in growing the animals and shipping them to the market.

The animal's immune system is primarily responsible for combatting the disease causing agents. Although very complicated and often poorly understood, the immune system's response generally involves the increased production and activation of macrophage cells which attack and destroy many of the disease causing agents. These macrophages are produced in various levels in the individual animal in response to a stimulus that results when a disease causing agent invades the animal's body. Often the activity of the individual macrophages and the number of macrophages produced in response to stimulus is insufficient to combat the invading agent; adverse disease symptoms, decrease in weight gain, or death often result. In addition, higher levels of activated macrophages present in the body prior to infection could help prevent the proliferation of the disease causing agents and the resulting disease.

Methods for stimulating the immune system to increase the number of activated macrophages available to combat animal diseases, particularly methods using natural agents such as proteins instead of chemical agents, are continually needed.

SUMMARY OF THE INVENTION

It is, therefore, an object of the present invention to provide a method for stimulating an animal's immune system.

It is another object of the present invention to provide a method for stimulating the production of macrophages.

It is another object of the present invention to provide a method for augmenting the oxidative metabolism, and therefore the production of reactive oxygen intermediates, by macrophages.

It is another object of the present invention to provide a method for preventing and treating infectious diseases caused by viruses, bacteria, fungi, protozoa, helminths, and the like.

It is a further object of the present invention to provide a composition for stimulating the immune system of an animal.

These and other objects are achieved by administering the proteins somatotropin (ST) and prolactin (PRL) to animals in amounts sufficient to stimulate the immune system by increasing the production of macrophages and augmenting the oxidative metabolism of macrophages.

In the preferred embodiment, ST or PRL are administered to animals in dosages from about 0.1-24 mg/animal/day to stimulate the production of macrophages and augment the oxidative metabolism of macrophages. These macrophages combat infectious disease causing agents such as viruses, bacteria, fungi, protozoa, helminths, and the like and thus are effective in preventing and treating diseases caused by those agents.

Other objects, advantages, and novel features of the present invention will become apparent from the following detailed description of the invention.

DETAILED DESCRIPTION OF THE INVENTION

According to the present invention, the proteins somatotropin (ST) or prolactin (PRL) are administered to animals in amounts sufficient to stimulate the immune system by increasing the production of macrophages and augmenting the oxidative metabolism of macrophages. These macrophages combat infectious disease causing agents such as viruses, bacteria, fungi, protozoa, helminths, and the like and thus are effective in preventing and treating diseases caused by those agents.

ST and PRL can be obtained from any suitable source. Methods for producing, isolating and purifying native and recombinant ST and PRL are well known in the field. ST and PRL as used herein includes all proteins having ST and PRL activity including natural, recombinant, mutein and analog proteins having deleted, replaced, or otherwise altered amino acid sequences. ST and PRL as used herein also includes the protein's biologically active and pharmaceutically acceptable salts, esters and other derivatives.

Preferably, ST or PRL administered to the animal is a ST or PRL obtained from the same species. However, ST or PRL for one species should stimulate the immune system in a closely related species. For example, it is believed that porcine ST will stimulate the immune system in bovines.

ST and PRL can be administered as in a composition containing a mixture of the protein in combination with pharmaceutically acceptable carriers such as various diluents and vehicles. The carrier can be any biocompatible and protein compatible carrier. Most preferably, the protein is mixed with pharmaceutically acceptable carriers to form a composition which allows for easy dosage preparation.

Although the dosages of ST and PRL vary according to the type of animal, age of the animal, size of the animal, type of infection, degree of infection, ST and PRL are typically administered to the animal in dosages from about 0.1-24 mg/animal/day to prevent and treat disease.

ST and PRL according to the present invention can be administered to the animal in any acceptable manner including by injection, using an implant, and the like. Injections are preferred because they permit precise control of the timing and dosage levels used for administration. ST and PRL according to the present invention are preferably administered parenterally. As used herein, parenteral administration means by intravenous, intramuscular, subcutaneous, or intraperitoneal injection, or by subcutaneous implant.

When administered by injection, ST and PRL according to the present invention can be administered to the animal in an injectable formulation containing any biocompatible and ST and PRL compatible carrier such as various vehicles, adjuvants, additives, and diluents. ST and PRL according to the present invention are added to the carrier in amounts sufficient to supply from about 0.1-24 mg/animal to the animal when injected. Preferably, ST and PRL according to the present invention are added to a buffer containing about 0.025 M $NaHCO_3$ and about 0.025 M $Na_2CO_3$ in amounts sufficient to supply from about 1-10 mg/animal.

Aqueous vehicles prepared from water having no nonvolatile pyrogens, sterile water, and bacteriostatic water and containing at least 0.025M buffer salts, such as sodium phosphate, sodium bicarbonate, sodium citrate, etc. are also suitable to form injectable ST and PRL solutions. In addition to these buffers, several other aqueous vehicles can be used. These include isotonic injection compositions that can be sterilized such as sodium chloride, Ringer's, dextrose, dextrose and sodium chloride, and lactated Ringer's. Addition of water-miscible solvents, such as methanol, ethanol, or propylene glycol generally increases solubility and stability of ST and PRL in these vehicles.

Nonaqueous vehicles such as cottonseed oil, sesame oil, or peanut oil and esters such as isopropyl myristate may also be used as suspension vehicles for ST and PRL compositions. Additionally, various additives which enhance the stability, sterility, and isotonicity of the composition including antimicrobial preservatives, antioxidants, chelating agents, and buffers can be added. Any vehicle, diluent, or additive used would, however, have to be biocompatible and compatible with ST and PRL according to the present invention.

ST and PRL according to the present invention can be administered to the animal in the form of a slow-release subcutaneous implant which is inserted beneath the skin of the animal. The implant can take the form of a pellet which slowly dissolves after being implanted in the animal or a biocompatible and animal compatible delivery module well known to those skilled in the art. Such well known dosage forms are designed such that the active ingredients are slowly released over a period of several days to several weeks. The implant is designed to deliver from about 0.1-24 mg/animal/day.

Although not preferred because the digestive system tends to inactivate proteins, ST and PRL can be administered orally if administered in a dosage form which prevents inactivation of the compounds by the digestive system. Such techniques and dosage forms are well known in the art; U.S. Pat. No. 4,639,435 to Fujii et al. discloses pharmaceutical compositions designed to deliver protein compounds orally without significant loss of bioactivity usually associated with oral administration.

ST and PRL according to the present invention are used to stimulate the production of macrophages and augment the oxidative metabolism of macrophages which combat infectious disease-causing agents such as viruses, bacteria, fungi, protozoa, helminths, and the like. The present invention is, therefore, useful for preventing and treating diseases caused by those agents in animals.

Any animal species susceptible to disease caused by these pathogenic disease causing agents can be administered ST and PRL according to the present invention. Human, bovine, porcine, canine, feline, equine, avian, and ovine are preferred, with livestock and poultry such as cattle, swine, sheep, chickens, and turkeys being most preferred.

Preventing or treating diseases such as Atrophic Rhinitis and Pleuropneumonia in swine, and Infectious Respiratory Tract Disease (IRD) and Mastitis in cattle are particular examples of possible uses for the present invention. Other possible uses for the present invention include resisting and inhibiting the growth of tumorous cells.

The invention having been generally described, the following examples are given as particular embodiments of the invention and to demonstrate the practice and advantages thereof. It is understood that the examples are given by way of illustration and are not intended to limit the specification or the claims to follow in any manner.

Example 1

Peripheral blood was collected from ten-week-old pigs and monocyte-derived mononuclear phagocytes were separated on a plasma Percoll gradient, as previously described in Musson, *Am. J. Path.* 111:331 (1983). These cells were washed twice in Hanks balanced salt solution (HBSS), adjusted to $2 \times 10^6$ cells/ml in Dulbecco's modified Eagle's medium (DMEM) supplemented with L-glutamine (2 mM), penicillin (50 U/ml), streptomycin (50 ug/ml) and two percent heat-inactivated fetal bovine serum and one ml was plated into 35-mm tissue culture wells. Following a two-hour incubation at 37° C. in a 5% $CO_2$ atmosphere, nonadherent cells were removed by washing with DMEM. Adherent cells (>90% α-naphthyl esterase positive) were incubated in fresh DMEM containing lipopolysaccharide (LPS) as a positive control (10 EU/ml) or various concentrations of pituitary-derived porcine somatotropin (pST), recombinant porcine somatotropin (rpST) or porcine pituitary-derived prolactin (npPRL). All tissue culture reagents and peptides were free of endotoxin (sensitivity of <0.01 EU/ml) as assessed by the chromagenic limulus ameobocyte lysate assay. Following a 24-hr incubation, $O_2-$ release was stimulated by the addition of 100 μl opsonized zymosan (Op-Zym, 1mg/ml) and determined spectrophotometrically by measuring superoxide dismutase-inhibitable reduction of ferricytochrome c and expressed as nMole $O_2-$/mg mononuclear phagocyte protein/hour. The results are shown in Table 1.

Referring to Table 1, in the absence of op-zym, mononuclear phagocytes released no $O_2-$. Normal mononuclear cells released only small amounts of $O_2-$ (36 nMole $O_2-$/mg protein/hour) when stimulated with opsonized zymosan. In contrast, the positive control LPS, which is a potent inducer of $O_2-$ (Edwards, *J. Immunol.*, 136:1820 1986), caused the release of 228 nMole $O_2-$/mg protein/hr. When mononuclear phagocytes were incubated with either pituitary-derived somatotropin or pituitary-derived prolactin and then stimulated with op-zym, there was a significant correlation between pST level and $O_2-$ release ($r=0.89$ and 0.88, respectively). These positive effects were not caused by contaminating peptides in the pituitary-derived preparations. Recombinant porcine somatotropin yielded a similar dose response curve to that of npST. Also the effect of 500 ng/ml pST or PRL was blocked by heat inactivated (56° C.) antibodies against pST or PRL, respectively. The results show that pituitary-derived porcine somatotropin (pST), recombinant porcine somatotropin (rpST), and pituitary-derived prolactin (pPRL) stimulate the production of reactive oxygen intermediates by macrophages. This increased macrophage activity increases the ability of the animal to combat viruses, bacteria, fungi, protozoa, helminths, and other disease causing agents. The proteins can, therefore, be used to prevent and treat infectious diseases.

Example 2

Alveolar macrophages (>98% α-naphthyl esterase positive) were obtained by pulmonary lavage and isolated by using known methodologies (McGuire et al., *J. Reticulo. Soc.*, 31:251 1982). Eight 10-day-old female pigs were anesthetized with Vetalor-Rompun (Parke-Davis, Nutley, NJ) at a dose of 0.4-0.8 mg/kg body weight before exsanguination and removal of the trachea and lungs. Sixty milliliters of sterile HBSS were instilled into the lungs with a rubber cannula connected to a syringe. The lungs were massaged gently, and the lavage fluids were collected and placed on ice. This lavage procedure was repeated four times. Cells were pelleted by centrifugation at 4° C. for 15 min at $400 \times g$, washed two times, allowed to adhere to plastic culture dishes, treated with pST or rpST for 24 hrs and then assayed for $O_2-$ release after stimulation with op-zym. The positive control was the supernatants from peripheral blood mononuclear cells that had been pretreated with ConA. These supernatants have been shown to have high levels of macrophage activating factors (Westly, et al., *Proc. Soc. Exp. Biol. Med.,* 45:2518, 1984). The results are shown in Table 2.

Referring to Table 2, the data were analyzed by a randomized incomplete block design (F=22.6,7,32 df,P<.001) and differences among treatments were detected with Duncan's New Multiple Range Test. Means with different superscripts are different (P<.05). Unstimulated alveolar macrophages generated 28 nMol $O_2-$/mg protein/hr. Op-zym stimulated the release of 199 nMol $O_2-$/mg protein/hr from alveolar macrophages, and this effect was totally blocked by superoxide dismutase. Significant enhancement of op-zym-induced $O_2-$ was caused by npST and rpST, as well as by the concanavalin A-conditioned supernatant. Furthermore, the enhancing effect of rpST was totally blocked by an antiserum that was specific for somatotropin. The data, therefore, shows that somatotropin primes alveolar macrophages for augmented $O_2-$ production thus enhancing their ability to combat respiratory tract diseases.

Example 3

One hundred-sixty-four hypophysectomized Sprague-Dawley rats were injected subcutaneously each day once daily with various concentrations of npST, rpST or pituitary-derived rat somatotropin (nrST) or with vehicle alone for nine consecutive days. Recombinant rat interferon-$\Gamma$ (IFN-$\Gamma$) which is a potent inducer of $O_2-$ in both in vitro and in vivo systems (Nathan et al., *J. Exp. Med.*, 158:160 1983 Edwards, *J. Immunol.*, 136:1820 1986) was used as a positive control. In order to obtain adequate cells for the subsequent analysis of $O_2-$, peritoneal macrophages from two rats were pooled. One way analysis of variance was used to analyze results of daily weight gain (F=184.1, 12,69 df,P<.001) and $O_2-$ production (F=13.6, 12,69 df,P<.001), and differences among means were detected by Duncan's New Multiple Range Test. The results are shown in Table 3.

Referring to Table 3, npST, rpST, and nrST caused a significant increase in growth rate, ranging from approximately 10% to 40% over the 10-day growth period. Macrophages from the two control groups (hypophysectomized-untreated and hypophysectomized-vehicle-treated) released no superoxide dismutase-inhibitable $O_2-$. In contrast, macrophages from hypophysectomized rats given recombinant rat IFN-$\Gamma$ released 417 nMole $O_2-$/mg protein/hr when stimulated with op-zym. Macrcphages from rats treated with pST or rpST demonstrated significant dose-related increases in $O_2-$ release on Op-zym stimulation. A similar effect was observed with rat ST, indicating that the effect was not simply due to the administration of an exogenous foreign protein.

The results from Examples 1-3 show that pST, rpST, and pPRL stimulate the production of macrophages and augment the oxidative metabolism of alveolar and peritoneal macrophages and peripheral blood mononuclear phagocytes. The increased activity of the macrophages enable them to combat infectious diseases caused by viruses, bacteria, fungi, protozoa, helminths, and other disease causing agents. These activated macrophages may also combat other inflammatory diseases and wound healing skin conditions.

Obviously many modifications and variations of the present invention are possible in light of the above teachings. It is therefore to be understood that within the scope of the appended claims the invention may be practiced otherwise than as specifically described.

TABLE 1

Effect of npST, rpST and npPRL on the Production of $O_2-$ in vitro by Porcine Peripheral blood-derived Macrophages.

| GROUP | NAME | nMole $O_2-$/mg[a] MEAN | SEM |
|---|---|---|---|
| 1 | Con(unsti) | 0 | 0 |
| 2 | Con/SOD | 0 | 0 |
| 3 | Con/ZYM | 36.4 | 18.2 |
| 4 | ZYM/SOD | 23.2 | 19.1 |
| 5 | LPS 10EU | 228.4 | 22.0 |
| 6 | LPS/SOD | 0 | 0 |
| 7 | nPRL 1ng | 42.2 | 2.1 |
| 8 | 10 | 53.4 | 6.4 |
| 9 | 50 | 66.0 | 34.9 |
| 10 | 100 | 450.4 | 37.8 |
| 11 | 500 | 837.9 | 14.0 |
| 12 | 1000 | 857.2 | 51.7 |
| 13 | 500 + AB | 106.8 | 71.1 |
| 14 | npST 1ng | 70.9 | 27.2 |
| 15 | 10 | 66.1 | 1.8 |
| 16 | 50 | 230.6 | 19.5 |
| 17 | 100 | 471.9 | 40.4 |
| 18 | 500 | 649.1 | 21.9 |
| 19 | 1000 | 488.7 | 34.1 |
| 20 | 500 + AB | 98.6 | 18.6 |
| 21 | rpST 1ng | 92.7 | 6.2 |
| 22 | 10 | 22.2 | 21.5 |
| 23 | 50 | 715.5 | 17.0 |
| 24 | 100 | 801.9 | 50.2 |
| 25 | 500 | 547.9 | 119.7 |
| 26 | 1000 | 757.3 | 44.6 |
| 27 | 500 + AB | 24.4 | 4.9 |

[a]macrophages were plated at $2.0 \times 10^6$ cells/35 mm dish in 5% $CO_2$, 2% fcs and 100% humidity. For each determination, a matched assay mixture containing Superoxide Dismutase (SOD) at a final concentration of 50 μg/ml was used. Data are from 2 separate experiments. Mean ± S.E. (n = 3).

TABLE 2

Effect of npST and rpST on porcine alveolar macrophages in vitro

| Treatment | nMol $O_2-$/mg protein/hr | SEM |
|---|---|---|
| Unstimulated | 28[a] | 14 |
| Stimulated with Op-Zym | 199[b] | 48 |
| Op-Zym + Superoxide Dismutase | 28[a] | 9 |
| Op-Zym + Con A supernatant | 418[c] | 76 |
| Op-Zym + npST (500 ng/ml) | 430[c] | 90 |
| Op-Zym + rpST (500 ng/ml) | 431[c] | 81 |
| Op-Zym + rpST + ST antibody | 48[a] | 20 |
| Op-Zym + ST antibody | 141[a,b] | 30 |

TABLE 3

Effect of npST, rpST, and native, pituitary-derived rat somatotropin (nrST) on the respiratory burst activity in rat peritoneal macrophages in vivo.

| Item | Number | Dose/ Rat/Day | Growth(G/Day) Mean | SEM | nMol $O_2-$/mg protein/hr Mean | SEM |
|---|---|---|---|---|---|---|
| Hypox Rats | 6 | — | 0.392[a] | 0.08 | −40[a] | 20 |
| + Vehicle | 11 | 200 ul | 0.282[a] | 0.05 | −17[a] | 7 |
| + Rat IFN-$\Gamma$ | 11 | 500 Units | 0.252[a] | 0.06 | 417[b] | 79 |
| + npST | 5 | 6 ug | 1.211[c] | 0.09 | 0[a] | 19 |
|  | 6 | 12 ug | 1.633[d] | 0.07 | 268[b] | 71 |

TABLE 3-continued

Effect of npST, rpST, and native, pituitary-derived rat somatotropin (nrST) on the respiratory burst activity in rat peritoneal macrophages in vivo.

| Item | Number | Dose/Rat/Day | Growth(G/Day) Mean | SEM | nMol $O_2^-$/mg protein/hr Mean | SEM |
|---|---|---|---|---|---|---|
| rpST | 5 | 24 ug | $2.060^{e,f,}$ | 0.05 | $438^b$ | 70 |
|  | 6 | 6 ug | $0.815^b$ | 0.03 | $-62^a$ | 14 |
|  | 6 | 12 ug | $1.067^{b,c,}$ | 0.07 | $280^b$ | 59 |
|  | 6 | 24 ug | $1.297^c$ | 0.07 | $344^b$ | 42 |
| + nrST | 5 | 12 ug | $1.850^{d,e,}$ | 0.11 | $3^a$ | 4 |
|  | 5 | 24 ug | $2.320^f$ | 0.10 | $267^b$ | 31 |
|  | 5 | 48 ug | $2.870^g$ | 0.10 | $247^b$ | 16 |
|  | 5 | 96 ug | $3.440^h$ | 0.10 | $309^b$ | 22 |

What is claimed is:

1. A method for treating diseases in an animal caused by infectious agents which are susceptible to attack by macrophages, comprising:

administering to said animal a disease treating amount of a protein selected from the group consisting of somatotropin and prolactin.

2. The method of claim 1 wherein said protein is administered in amounts of from about 0.1-24 mg/animal/day.

3. The method of claim 1 wherein said protein is administered parenterally.

4. The method of claim 3 wherein said protein is administered using an implant, said implant further comprising:

a biocompatible and said protein compatible implant material; and a disease treating amount of said protein.

5. The method of claim 1 wherein said protein is administered in an injectable formulation, said injectable formulation further comprising:

a biocompatible and said protein compatible carrier; and a disease treating amount of said protein.

6. The method of claim 5 wherein said carrier is a buffer containing about 0.025 M $NaHCO_3$ and about 0.025 M $Na_2CO_3$.

7. The method of claim 1 wherein said protein is a recombinant protein.

* * * * *